United States Patent [19]

Edwards et al.

[11] Patent Number: 5,456,682
[45] Date of Patent: Oct. 10, 1995

[54] ELECTRODE AND ASSOCIATED SYSTEMS USING THERMALLY INSULATED TEMPERATURE SENSING ELEMENTS

[75] Inventors: Stuart D. Edwards, Los Altos; Roger A. Stern, Cupertino, both of Calif.

[73] Assignee: EP Technologies, Inc., Sunnyvale, Calif.

[21] Appl. No.: 191,055

[22] Filed: Feb. 2, 1994

Related U.S. Application Data

[63] Continuation of Ser. No. 37,740, Mar. 26, 1993, abandoned, which is a continuation of Ser. No. 790,578, Nov. 8, 1991, abandoned.

[51] Int. Cl.⁶ ................................................. A61B 17/36
[52] U.S. Cl. ................................. 606/31; 606/28; 128/736
[58] Field of Search ................................. 606/29, 30, 31, 606/28, 27; 128/736, 742; 374/141, 152; 364/557; 607/97, 100, 101, 102, 154

[56] References Cited

U.S. PATENT DOCUMENTS

| | | | |
|---|---|---|---|
| 4,196,734 | 4/1980 | Harris | 606/31 |
| 4,271,837 | 6/1981 | Schuler | 606/39 |
| 4,397,314 | 8/1983 | Vaguine | 128/399 |
| 4,448,547 | 5/1984 | Wickersheim | 374/131 |
| 4,681,122 | 7/1987 | Winters et al. | 128/736 |
| 4,691,703 | 9/1987 | Auth et al. | 606/31 |
| 4,692,685 | 9/1987 | Blaze . | |
| 4,800,899 | 1/1989 | Elliott | 128/804 |
| 4,805,621 | 2/1989 | Heinze et al. . | |
| 4,813,429 | 3/1989 | Eshel et al. . | |
| 4,860,744 | 8/1989 | Johnson et al. . | |
| 4,907,589 | 3/1990 | Cosman | 606/34 |
| 4,938,761 | 7/1990 | Ensslin | 606/51 |
| 4,945,912 | 8/1990 | Langberg . | |
| 4,955,377 | 9/1990 | Lennox et al. | 128/401 |
| 4,960,109 | 10/1990 | Lele | 128/736 |
| 4,966,597 | 10/1990 | Cosman . | |
| 4,967,765 | 11/1990 | Turner et al. . | |
| 4,979,948 | 12/1990 | Geddes et al. | 606/33 |
| 4,998,933 | 3/1991 | Eggers et al. | 606/41 |
| 5,006,119 | 4/1991 | Acker et al. | 606/27 |
| 5,026,366 | 6/1991 | Leckrone . | |
| 5,035,694 | 7/1991 | Kasprzyk et al. | 606/27 |
| 5,050,597 | 9/1991 | Daikuzono . | |
| 5,057,105 | 10/1991 | Malone et al. | 606/28 |
| 5,057,106 | 10/1991 | Kasevich et al. | 606/33 |
| 5,084,044 | 1/1992 | Quint | 606/27 |
| 5,114,423 | 5/1992 | Kasprzyk et al. | 606/27 |
| 5,122,137 | 6/1992 | Lennox | 606/40 |
| 5,193,526 | 3/1993 | Daikuzono . | |
| 5,233,515 | 8/1993 | Cosman . | |

FOREIGN PATENT DOCUMENTS

3838840   5/1990   Germany ............................. 606/31

*Primary Examiner*—Stephen C. Pellegrino
*Assistant Examiner*—Guy Tucker
*Attorney, Agent, or Firm*—Ryan, Maki & Hohenfeldt

[57] ABSTRACT

An ablation electrode carries a temperature sensing element for measuring the temperature of the tissue being ablated. A thermal insulating element associated with the sensing element blocks the transfer of heat energy from between the temperature sensing element and the body. The temperature sensing element therefore measures temperature without being affected by the surrounding thermal mass of the electrode.

18 Claims, 8 Drawing Sheets

ELECTRODE AND ASSOCIATED SYSTEMS USING THERMALLY INSULATED TEMPERATURE SENSING ELEMENTS

This is a continuation of application Ser. No. 08/037,740, filed on Mar. 26, 1993 (abandoned) which is a continuation of Ser. No. 07/790,578, filed Nov. 8, 1991 (abandoned).

FIELD OF THE INVENTION

The invention generally relates to catheters and associated power sources. In a more specific sense, the invention relates to ablation catheters that, once steered and manipulated within interior regions of the body, transmit energy to form lesions for therapeutic purposes.

BACKGROUND OF THE INVENTION

Physicians make use of catheters today in medical procedures to gain access into interior regions of the body to ablate targeted tissue areas. It is important for the physician to control carefully and precisely the emission of energy within the body used to ablate the tissue.

The need for careful and precise control over the catheter is especially critical during procedures that ablate tissue within the heart. These procedures, called electrophysiological therapy, are becoming more widespread for treating cardiac rhythm disturbances.

During these procedures, a physician steers a catheter through a main vein or artery (which is typically the femoral artery) into the interior region of the heart that is to be treated. The physician then further manipulates a steering mechanism to place the electrode carried on the distal tip of the catheter into direct contact with the tissue that is to be ablated. The physician directs radio frequency energy from the electrode tip through tissue to an indifferent electrode to ablate the tissue and form a lesion.

Cardiac ablation especially requires the ability to precisely monitor and control the emission of energy from the ablation electrode.

SUMMARY OF THE INVENTION

The invention provides ablation electrodes and associated systems having improved tissue temperature sensing capabilities. The improved temperature sensing capabilities enhance system control functions based upon tissue temperature.

The ablation electrode comprises an energy emitting body. A temperature sensing element is located on the body. The element senses the temperature of the tissue being ablated by the electrode.

According to the invention, the electrode includes a thermal insulating element located between the body and the temperature sensing element. The insulating element blocks the transfer of heat energy from between the temperature sensing element and the body.

In one embodiment, the electrode body carries multiple temperature sensing elements. At least one, and preferable all, the temperature sensing elements are thermally insulated.

A system incorporating the electrode as above described includes a monitor that measures tissue temperature using the thermally isolated temperature sensing elements located on the electrode.

The thermally insulated temperature sensing element measures true tissue temperature, without being affected by the surrounding thermal mass of the electrode.

DESCRIPTION OF THE PREFERRED EMBODIMENTS

Figure 1:
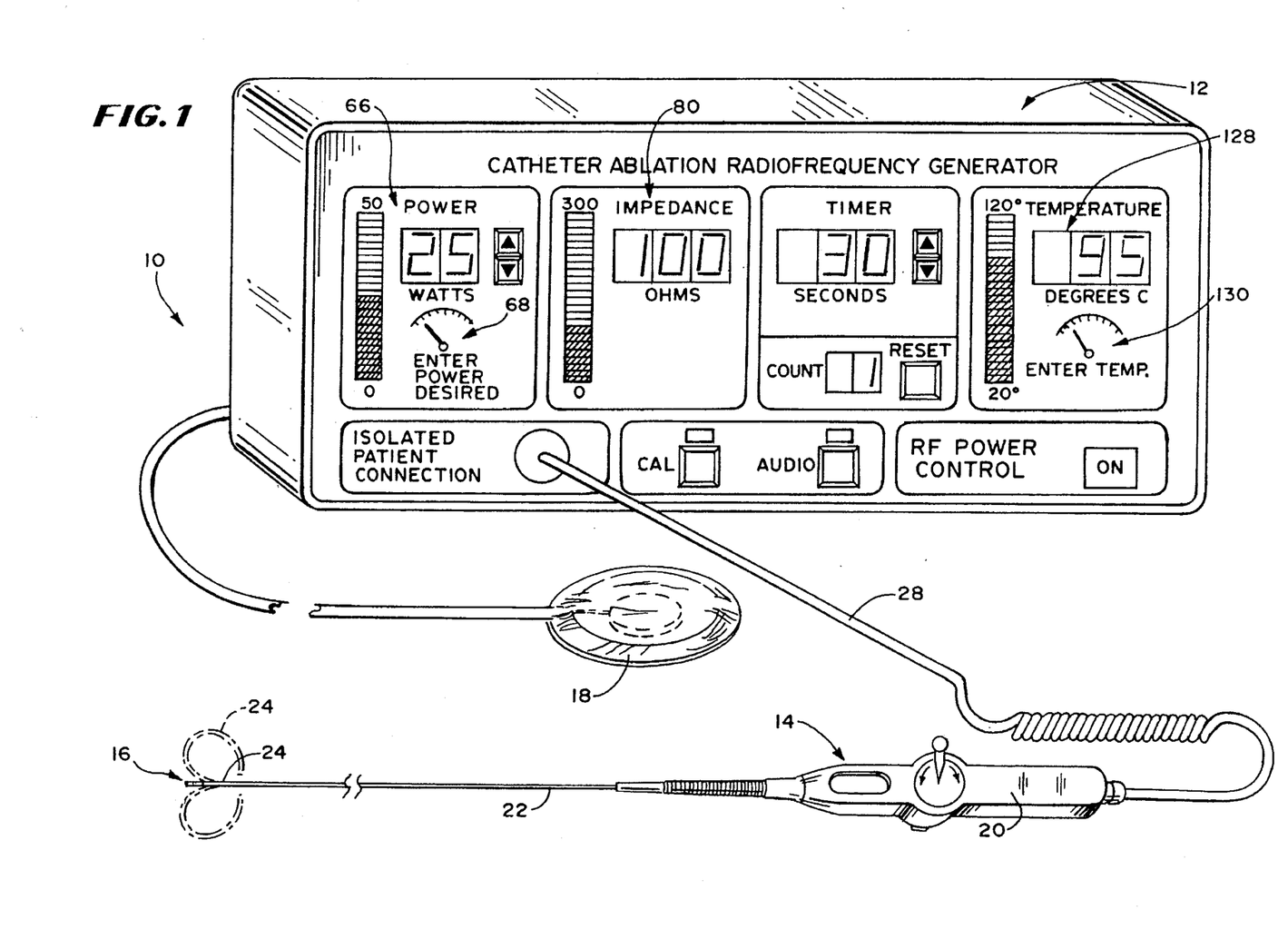
FIG. 1 is a perspective view of a system for ablating tissue that embodies the features of the invention.

FIG. 1 shows a system 10 for performing ablation on human tissue that embodies the features of the invention. The system 10 includes a radiofrequency generator 12 that delivers radiofrequency energy. The system 10 also includes a steerable catheter 14 carrying a radiofrequency emitting tip electrode 16.

In the illustrated embodiment, the system 10 operates in a monopolar mode. In this arrangement, the system 10 includes a skin patch electrode that serves as an indifferent second electrode 18. In use, the indifferent electrode 18 attaches to the patient's back or other exterior skin area.

Alternatively, the system 10 can be operated in a bipolar mode. In this mode, the catheter 14 carries both electrodes.

In the illustrated embodiment, the ablation electrode 16 and indifferent electrodes 18 are made of platinum.

The system 10 can be used in many different environments. This specification describes the system 10 when used to provide cardiac ablation therapy.

When used for this purpose, a physician steers the catheter 14 through a main vein or artery (typically the femoral artery) into the interior region of the heart that is to be treated. The physician then further manipulates the catheter 14 to place the tip electrode 16 into contact with the tissue within the heart that is targeted for ablation. The user directs radio frequency energy from the generator 12 into the tip electrode 16 to form a lesion on the contacted tissue.

In the embodiment shown in FIG. 1, the catheter 14 includes a handle 20, a guide tube 22, and a tip 24, which carries the tip electrode 16 (which also will be called the ablation electrode). The handle 20 encloses a steering mechanism 26 for the catheter tip 24. A cable 28 extending from the rear of the handle 20 has plugs (not shown). The plugs connect the catheter 14 to the generator 12 for conveying radiofrequency energy to the ablation electrode 16. The radiofrequency heats the tissue to form the lesion.

Left and right steering wires (not shown) extend through the guide tube 22 to interconnect the steering mechanism 26 to the left and right sides of the tip 24. Rotating the steering mechanism 26 to the left pulls on the left steering wire, causing the tip 24 to bend to the left. Also, rotating the steering mechanism 26 to the right pulls on the right steering wire, causing the tip 24 to bend to the right. In this way, the physician steers the ablation electrode 16 into contact with the tissue to be ablated.

Figures 2, 2A:
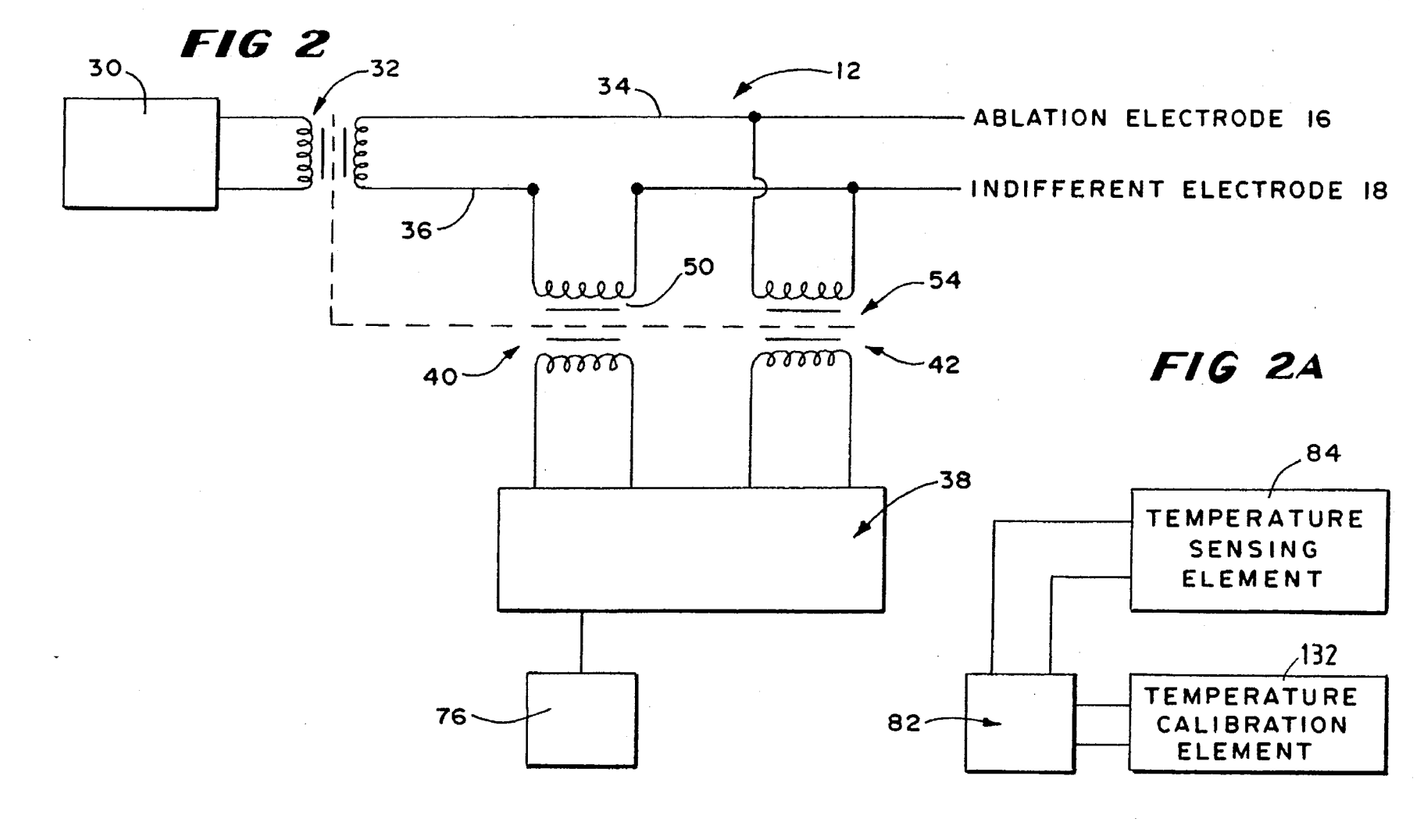
FIG. 2 is a schematic view of the generator and associated monitor and control circuits for the system.
FIG. 2A is a schematic view of the temperature monitoring circuit and its associated calibration system.

The generator 12 includes a radiofrequency power source 30 connected through a main isolation transformer 32 to first and second conducting lines 34 and 36.

In the illustrated environment, the power source 30 delivers up to 50 watts of power at a frequency of 500 kHz. The first conducting line 34 leads to the ablation electrode 16. The second conducting line 36 leads to the indifferent patch electrode 18.

Monitoring Actual and Apparent Radiofrequency Power

Figure 3:
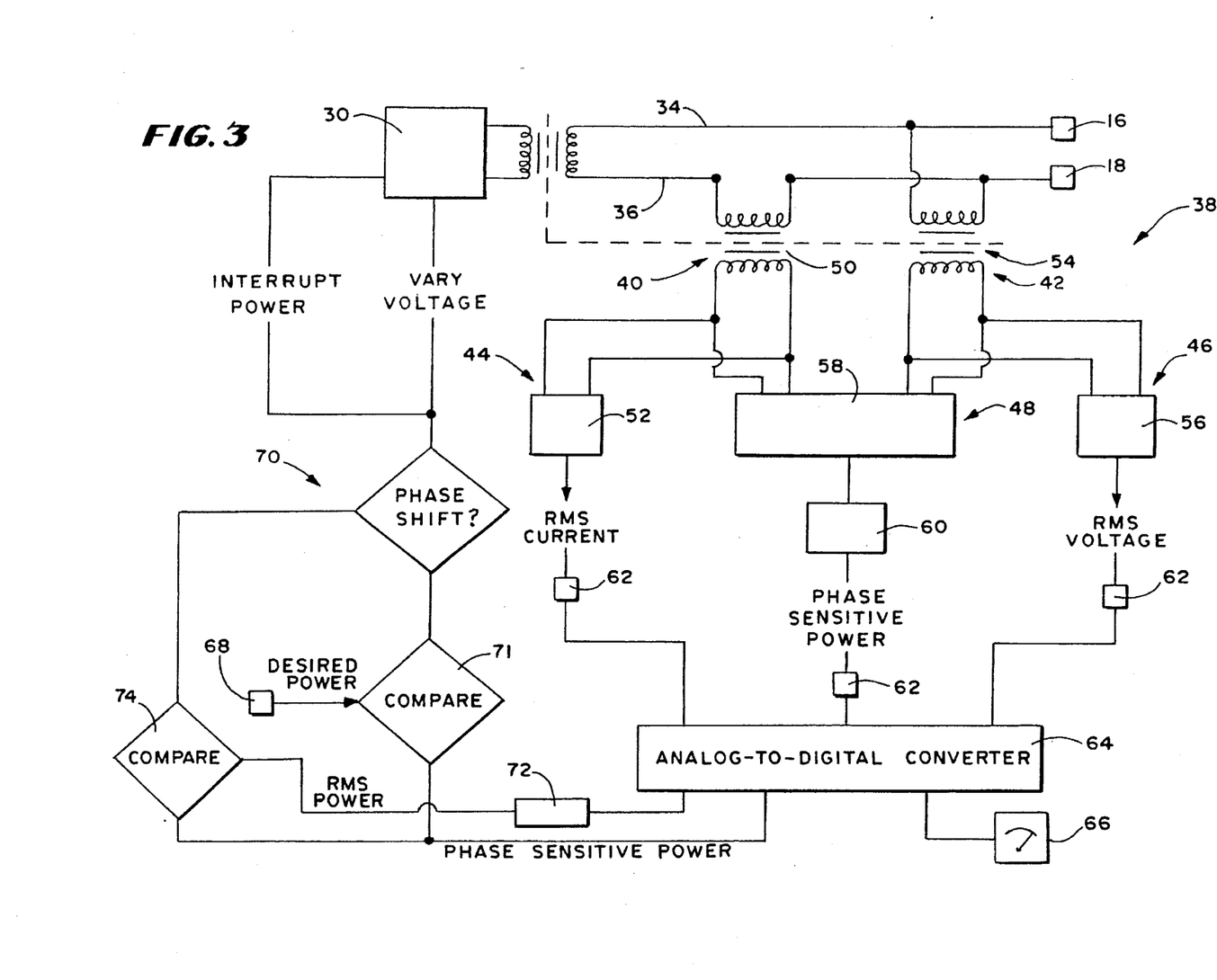
FIG. 3 is a schematic view of the power monitor and control circuit for the system.

As FIGS. 2 and 3 show, the system 10 includes first monitoring means 38 for measuring the radiofrequency current and radiofrequency voltage delivered by the generator 12 to the patient. The first monitoring means 38 also derives control signals indicative of RMS (root mean squared) voltage (in volts), RMS current (in amps), and actual phase sensitive power (in watts) to support other control functions of the generator 12.

The first monitoring means 38 may be variously configured and constructed. In the illustrated embodiment, the first monitoring means 38 includes current monitoring means 40 for measuring the radiofrequency current passing from the first line 34 through the tissue to the second line 36 (i.e., from the ablation electrode 16 to the indifferent patch electrode 18).

The first monitoring means 38 also includes voltage monitoring means 42. The voltage monitoring means 42 measures the radiofrequency voltage generated between the first and second conducting lines 34 and 36 (i.e., between the ablation electrode 16 and the indifferent patch electrode 18).

The first monitoring means 38 includes three control outputs 44, 46, and 48.

The first control output 44 carries a signal representative of RMS current conducted by the ablation electrode 16.

The second control output 46 carries a signal representative of the RMS voltage between the ablation electrode 16 and the indifferent patch electrode 18.

The third control output 48 carries a signal representative of actual phase sensitive power transmitted by the ablation electrode 16.

In the illustrated embodiment (as FIGS. 2 and 3 show), the current monitoring means 40 includes an isolated current sensing transformer 50 connected in the second conducting line 36. In this arrangement, the current sensing transformer 50 directly measures the radiofrequency current passing through the ablation electrode 16 to the indifferent patch electrode 18.

The measured value is a radiofrequency signal varying at the selected rate, which in the illustrated embodiment is 500 kHz.

The current sensing transformer 50 is connected to the first control output 44, which derives RMS current. The first control output 44 includes an integrated circuit RMS converter 52 to do this function. The RMS current converter first squares the radiofrequency current input signal from the current sensing transformer 50, and then averages the squared signal over a user prescribed period (which in the illustrated embodiment is about once every 0.01 second). The RMS current converter 52 then takes the square root of the average squared value. The resulting output represents RMS current.

The RMS current signal takes the form of a relatively slowly varying signal, compared with the rapidly varying radiofrequency current input signal.

As FIGS. 2 and 3 show, the voltage monitoring means 42 includes an isolated voltage sensing transformer 54 that is connected between the first and second conducting lines. In this arrangement, the voltage sensing transformer 54 directly measures the radiofrequency voltage across the body tissue between the ablation electrode 16 and the indifferent patch electrode 18.

Like the value measured by the current sensing transformer 50, the measured voltage value is a radiofrequency signal varying at the selected 500 kHz rate.

The voltage sensing transformer 54 is connected to the second control output 46, which derives RMS voltage. The second control output 46 includes an integrated circuit RMS converter 56 to do this function. The RMS voltage converter 56 squares the radiofrequency voltage input signal and then averages it over the same user prescribed period used by the current converter 52. The RMS voltage converter 56 then takes the square root of the average squared voltage value.

The resulting RMS voltage signal (like the RMS current signal) takes the form of a relatively slowly varying signal.

The voltage sensing transformer 54 is also connected to the third control output 48, which derives actual phase sensitive power. The third control output 48 includes an analog multiplier integrated circuit 58 to do this function. The multiplier circuit 58 receives as one input the radiofrequency input current signal directly from the current sensing transformer 50. The multiplier circuit 58 also receives as a second input the radiofrequency input voltage signal directly from the voltage sensing transformer 54.

The output of the multiplier circuit 58 is the product of these two inputs, which represents the actual radiofrequency power transmitted by the ablation electrode 16.

The power value is (like its component current and voltage inputs) a radiofrequency signal varying at a relatively high radiofrequency rate.

The third control output 48 also includes a low pass filter 60. In the illustrated embodiment, which operates with a radiofrequency rate of 500 kHz, the cut off frequency of the filter 60 selected is about 100 Hz. The rapidly varying measured input power value is low pass filtered by the filter 60 into a relatively slowly varying signal.

This signal represents the actual phase sensitive power signal of the radiofrequency energy that the ablation electrode 16 delivers to the targeted tissue.

The first, second, and third control outputs 44, 46, and 48 each includes appropriate inline scaling circuits 62. The scaling circuits 62 scale the RMS current signal, the RMS voltage signal, and the actual phase sensitive power signal to a specified voltage range that can be usable by the remainder of generator 12 circuitry. In the illustrated embodiment, the scaled range is 0.0 to 5.0 volts.

The first monitoring means 38 also includes an analog to digital converter 64. The converter 64 digitizes a selected one or more of the analog RMS current output signal, RMS voltage output signal, and the actual phase sensitive power signal.

The digital output(s) of the converter 64 can be used to display measurement results. In the illustrated embodiment, the system 10 includes a first digital display 66 on the generator 12 to show the user the actual phase sensitive power signal.

The digital output(s) of the converter 64 also can be used to control operation of the generator 12. In the illustrated embodiment, the system 10 uses the digitized outputs in a feedback loop that maintains radiofrequency output voltage within a desired range or at a constant value to control radiofrequency power at the ablation electrode 16. By controlling the power delivered by the generator 12, the physician can reproducibly form lesions of the desired depth during an ablation procedure.

In this arrangement, the system 10 includes an input 68 for the user to enter an operating value desired for the actual phase sensitive power for the generator 12. The system 10 includes power control means 70 that includes comparator 71 to compare desired power with actual phase sensitive power. The output of the comparator varies the output voltage of radiofrequency power source 30 to maintain minimum error between the measured actual power and the set point power.

In the illustrated embodiment, the power control means 70 also monitors phase differences between radiofrequency voltage and current. The power control means 70 does this function by computing apparent power and by comparing the computed apparent power to the actual phase sensitive power. If the radiofrequency voltage and current signals are exactly in phase, the apparent power and actual phase sensitive power will be the same. However, if there is a phase difference, actual phase sensitive power will differ from the apparent power by a factor that represents the cosine of the phase angle.

In the illustrated embodiment, the power control means 70 includes a multiplier circuit 72 that obtains the product of the RMS current and RMS voltage. The resulting output of the multiplier circuit 72 forms the apparent (i.e., not phase sensitive) power of the system 10. The power control means 70 includes a comparator 74 to compare the derived apparent power with the actual phase sensitive power. The magnitude of the output of the comparator 74 quantifies the amount of the phase shift.

If the output of the phase shift comparator 74 exceeds a preselected amount, the power control means 70 generates a warning signal to show that a phase shift between the radiofrequency voltage and current has occurred. The system 10 may include a flashing light and audible alarm (not shown) to warn the user.

The power control means 70 operates to maintain a constant set power when the output of the phase shift comparator 74 remains within an allowable range above the threshold amount. The power control means 70 operates to reduce the output voltage of the source 30 when the output of the phase shift comparator 74 increases beyond this range. If the output of the phase shift comparator 74 shows a phase shift beyond a maximum threshold value, the power control means 70 generates a signal to shut off all power to the ablation electrode 16.

Monitoring Tissue Impedance

Figure 4:
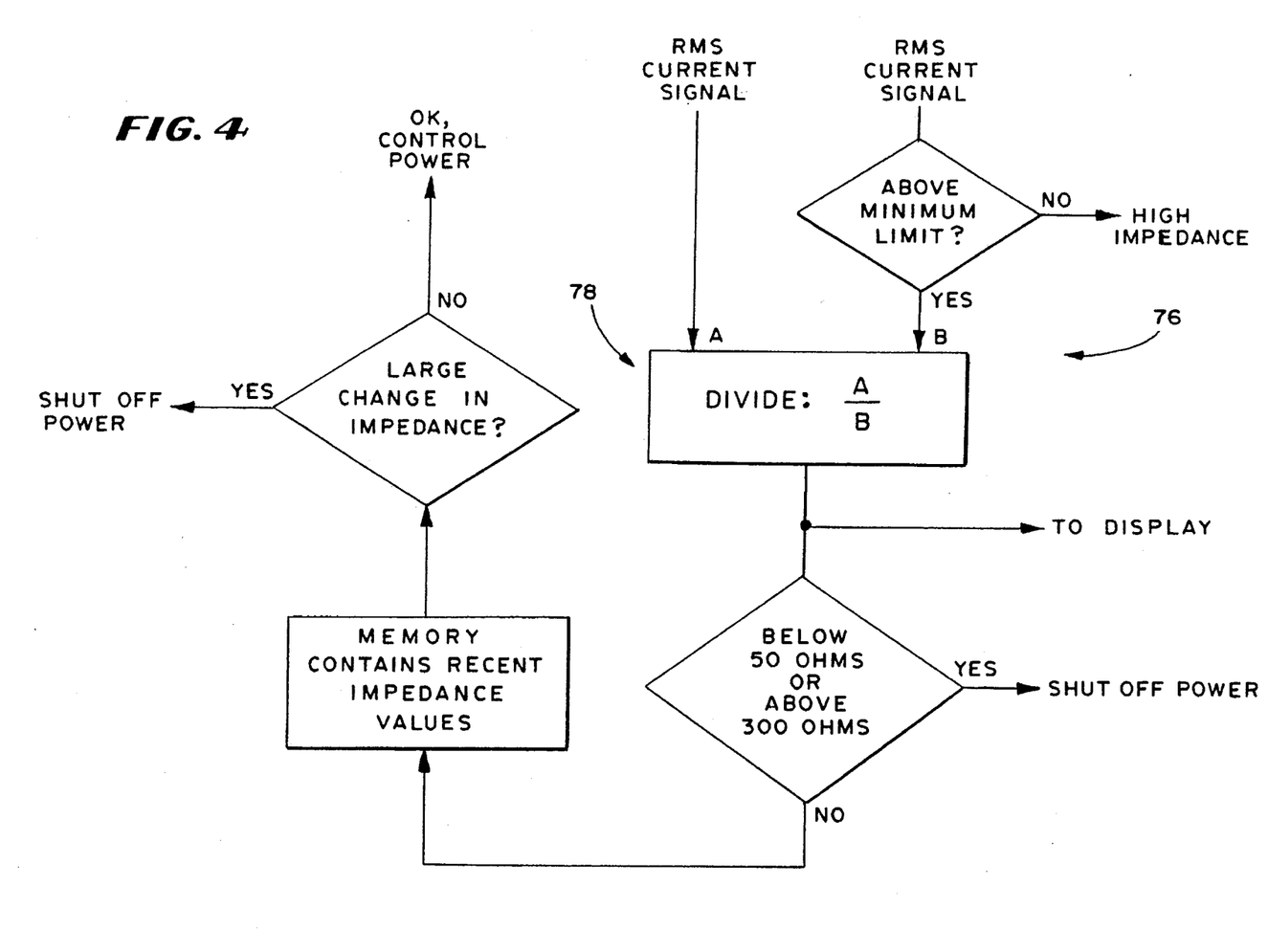
FIG. 4 is a schematic view of the tissue impedance monitor and control circuit for the system.

As FIG. 4 shows, the system 10 further includes second monitoring means 76 for deriving the impedance of the tissue undergoing ablation. The second monitoring means 76 derives tissue impedance not only in absolute terms, but it also serves to record changes in tissue impedance over time.

The second monitoring means 76 generates appropriate control signals based upon observed absolute values of tissue impedance as well as sensed changes according to preprogrammed criteria.

The second monitoring means 76 may be variously configured and constructed. In the illustrated embodiment, the second monitoring means 76 includes a microprocessor 78. The microprocessor 78 samples the digitized outputs of the analog-to-digital converter 64 at prescribed intervals (for example, every 20 milliseconds, which represents a 50 Hz sampling rate).

The microprocessor 78 also divides the sampled digitized RMS voltage signal by the sampled digitized RMS current signal. The digital result is the tissue impedance (in ohms) for the sample. Preferably, the system 10 includes a second display 80 on the generator 12 that shows the user the sampled tissue impedance.

The microprocessor 78 also maintains a record of sampled tissue impedances over time. From this record, the microprocessor 78 calculates the changes in tissue impedance during a selected interval and generates appropriate control signals based upon predetermined criteria.

The predetermined criteria under which the microprocessor 78 generates the control signals based upon tissue impedance can vary. Preferably, the tissue impedance control signals are used to augment the monitoring and control functions of the power control means 70 just described.

In the illustrated embodiment, if measured tissue impedance falls outside a predetermined set range, the microprocessor 78 generates a command signal to shut off power to the ablation electrode 16, whatever the actual phase sensitive power level sensed. The set range for tissue impedance for a cardiac ablation procedure is believed to be about 50 to 300 ohms.

When tissue impedance begins in the set range and, over time, increases beyond it, the most likely cause is the coagulation of blood on the ablation electrode 16. A sudden rise in tissue impedance over the set range suggests the sudden onset of coagulation or a sudden shift in the position of the ablation electrode 16. Rapid fluctuations of the tissue impedance also could suggest poor contact between the ablation electrode 16 and the targeted tissue. All require prompt response; for example, withdrawal and cleaning of the ablation electrode 16, or repositioning of the ablation electrode 16.

The system 10 preferably includes flashing lights and an audible alarm (not shown) to transmit a warning to the user when these conditions occur.

A very high tissue impedance value could suggest poor skin contact with the indifferent electrode 18, or an electrical problem in the system 10. Again, this calls for prompt corrective action.

If tissue impedance remains within the set range, but rises beyond a prescribed amount within the range, the second monitoring means 76 generates a control signal that reduces but does not interrupt, the power output. In this arrangement, a relatively tight range of tissue impedance can be established (for example, 80 to 150 ohms) to maintain relatively constant power within this range.

Monitoring Tissue Temperature

Figures 5A, 5B:
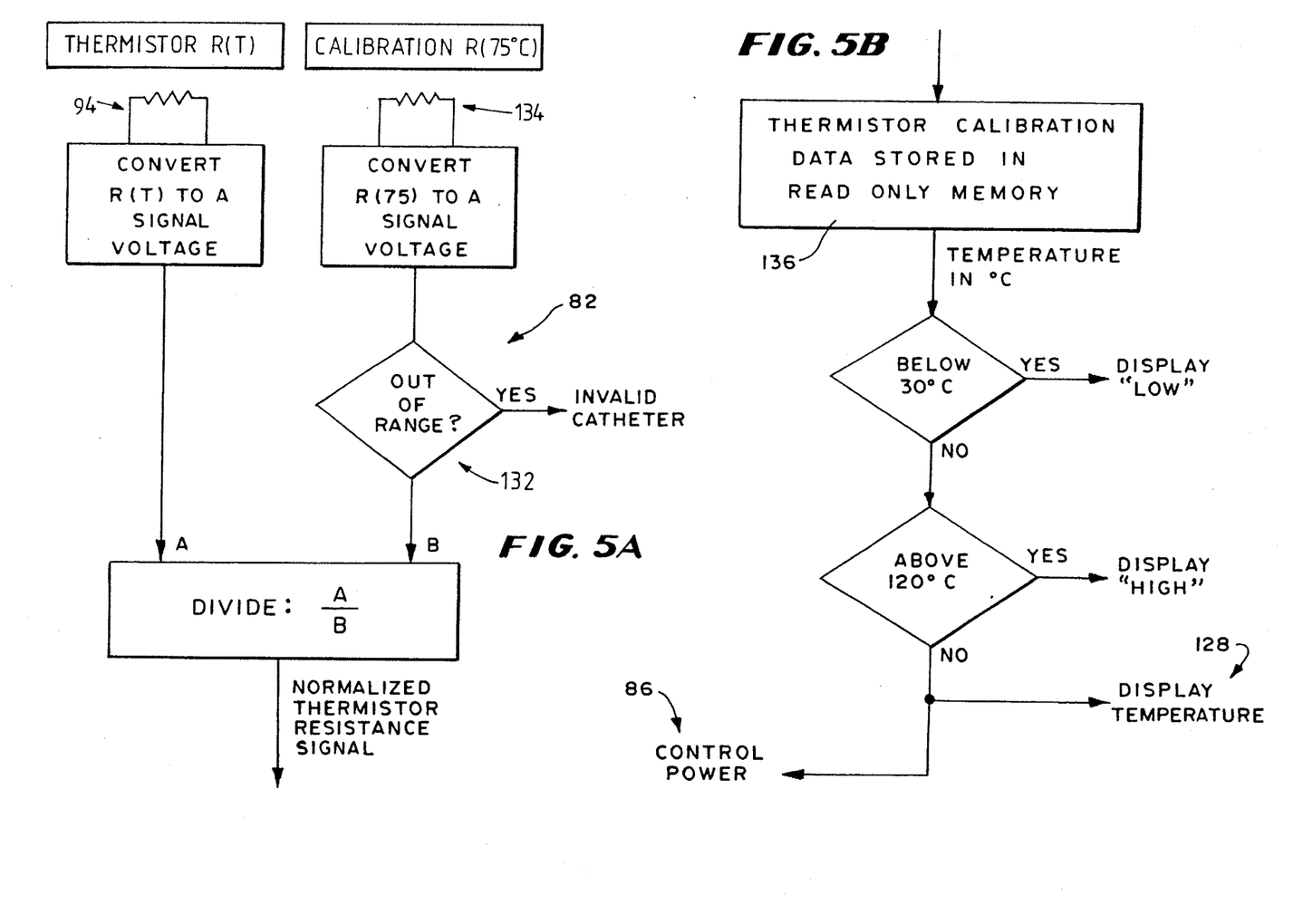
FIGS. 5A and 5B is a schematic view of the tissue temperature monitor and control circuit for the system.

As FIG. 5 shows, the system 10 includes third monitoring means 82 for sensing the temperature of the tissue in contact with the ablation electrode 16. The third monitoring means 82 includes temperature sensing means 84 carried in the ablation electrode 16. The system 10 also includes control means 86 for the generator 12 that is responsive to the sensed tissue temperature for performing generator control functions.

Thermal insulation means 88 thermally isolates the temperature sensing means 84 from the thermal mass of the ablation electrode 16. Thus, the temperature sensing means 84 does not add to or serve as a part of the thermal mass of the ablation electrode 16. It serves to show the true temperature of the tissue with which it is in contact, without adding to the thermal mass of the ablation electrode 16 and without being influenced by the temperature of the surrounding thermal mass of the ablation electrode 16.

Figure 6A:
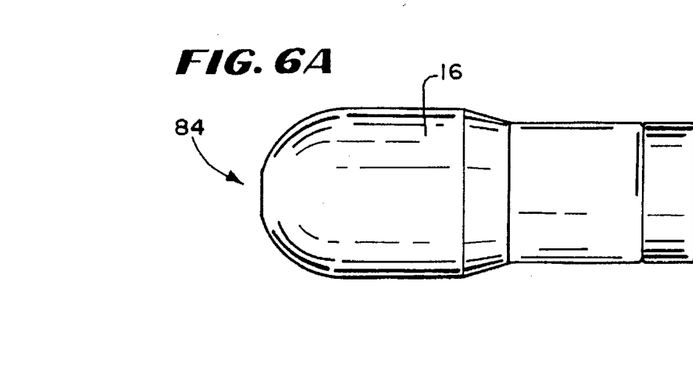
FIGS. 6A to C are views of an electrode with thermally insulated temperature sensing element that can be used in associated with the system to measure tissue temperature.
Figure 6B:
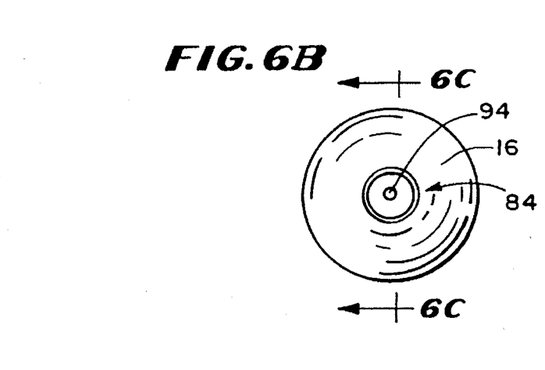
Figure 6C:
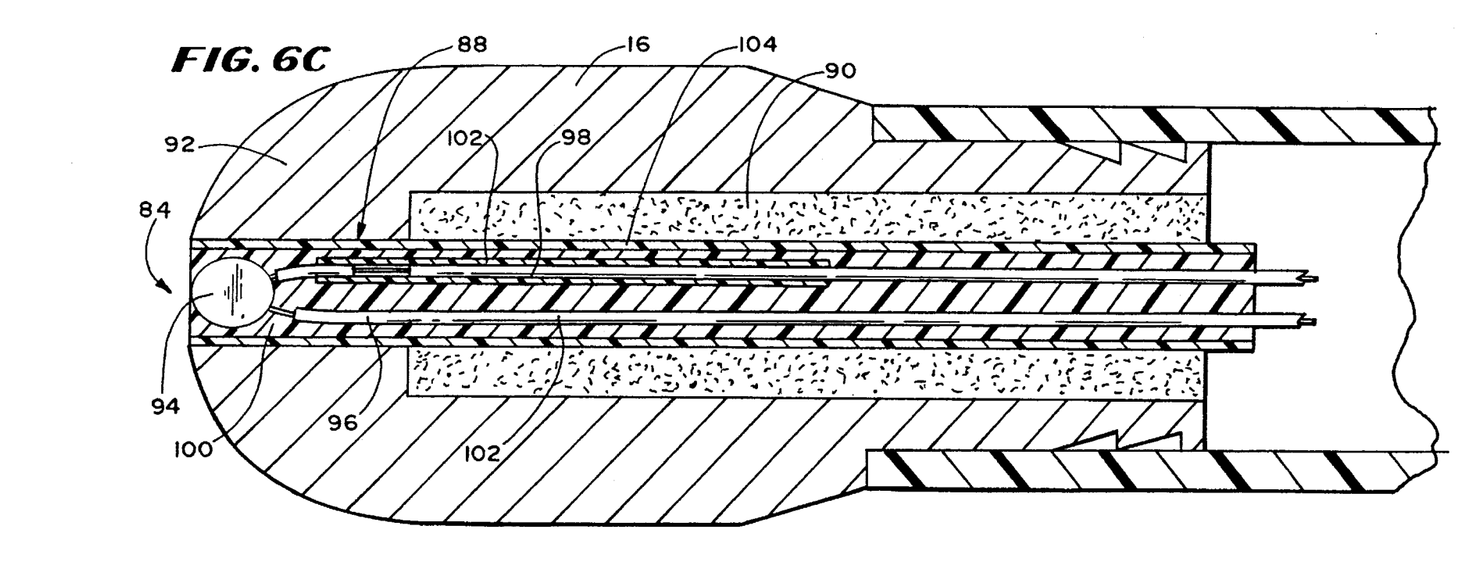

In the embodiment illustrated in FIGS. 6A to C, the ablation electrode 16 includes an interior well 90 at its tip end 92. The temperature sensing means 84 occupies this well.

In this arrangement, the thermal insulating means 88 isolates the temperature sensing means 84 from the interior surface of the well 90 and the rest of the thermal mass of the ablation electrode 16.

In FIGS. 6A to C, the temperature sensing means 84 includes a small bead thermistor 94 with two associated lead wires 96 and 98. The temperature sensing tip of the thermistor 94 is exposed at the tip end 92 of the ablation electrode 16 for tissue contact.

In the illustrated embodiment (see FIGS. 2A and 5A and B), the third monitoring means 82 includes means 132 for calibrating the thermistor 94 to account for deviations in nominal resistance among different thermistors 94. During manufacture of the catheter 10, the resistance of thermistor 94 is measured at a known temperature; for example, 75 degrees C. A calibration resistor 134 equal to the measured value is incorporated into the catheter handle 20. The leads of the calibration resistor 134 are connected to the third monitoring means 82.

The thermistor 94 of the type shown is commercially available from the Fenwal Co. (Massachusetts) under the trade designation 111-202CAKBD1. The lead wires 96 and 98 comprise #36 AWG signal wire Cu+ clad steel (heavy insulation).

Potting compound 100 encapsulates the thermistor 94 and lead wires 96 and 98 within the electrode well. Insulating sheathes 102 also shields the encapsulated lead wires 96 and 98. Together, the compound 100 and sheathes 102 electrically insulate the thermistor 94 from the surrounding ablation electrode 16.

The potting compound 100 and insulation sheathes 102 can be made with various materials. In the illustrated embodiment, loctite adhesive serves as the potting compound 100, although cyanoacrylate adhesive or RTV adhesive and the like could be used. The sheathes 102 are made from polymide material, although other conventional electrical insulating materials also can be used.

In the illustrated embodiment, the thermal insulating means 88 comprises a tube 104 that envelopes the encapsulated thermistor 94 and lead wires 96 and 98. The thermal insulation tube 104 is itself adhesive bonded to the interior wall of the well 90.

The thermal insulating material of the tube 104 can vary. In the illustrated embodiment, it is a polymide material having a wall thickness of about 0.003 inch. Other thermal insulating materials like mylar or kapton could be used.

The lead wires 96 and 98 for the thermistor 94 extend from the electrode well 90 through the guide tube 22 and into the catheter handle 20. There, the lead wires 96 and 98 electrically couple to the cable 28 extending from the handle 20. A cable plug (not shown) connects to the generator 12 and transmits the temperature signal from the thermistor 94 to the third monitoring means 82.

Figure 7A:
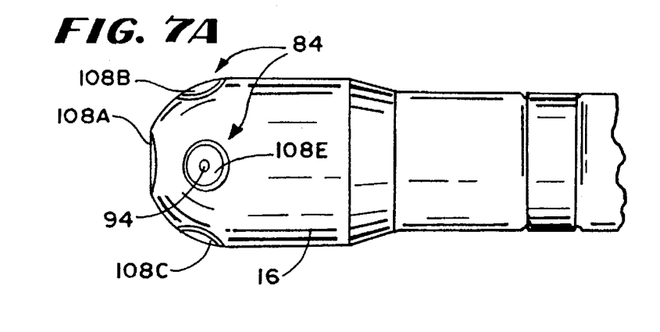
FIGS. 7A to C are views of an electrode with multiple thermally insulated temperature sensing elements that can be used in associated with the system to measure tissue temperature.
Figure 7B:
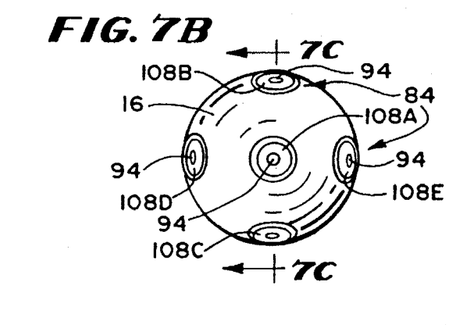
Figure 7C:
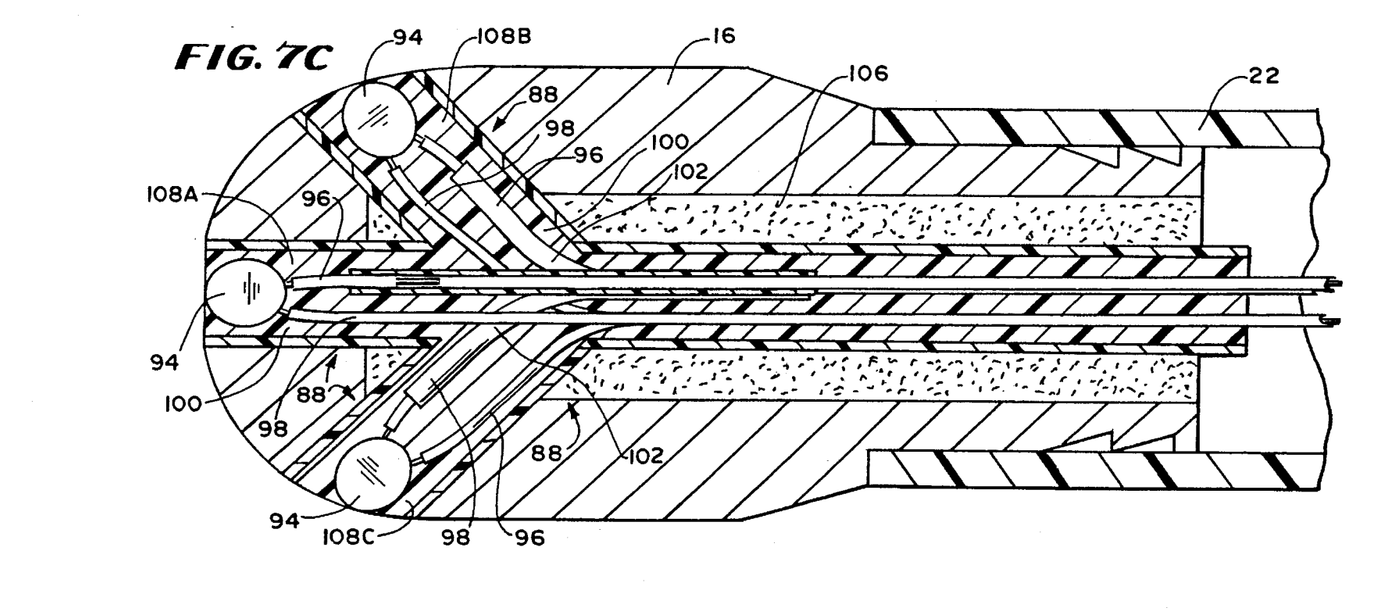

FIGS. 7A to C show an alternate embodiment of an ablation electrode 16 having an array of temperature sensing means 84. At least one temperature sensing means 84, and preferably all of them, are thermally isolated from the ablation electrode 16 in the manner shown in FIGS. 6A to C.

As FIGS. 7A to C show, the ablation electrode 16 in the multiple array version includes an interior core well 106. Five branch wells 108A to E extend from the core well 106. The branch wells 108A to E open at the surface of the ablation electrode 16. One branch well 108A opens at the tip of the ablation electrode 16, like the single temperature sensing means 84 shown in FIGS. 6A to C. The other four branch wells 100B to E extend at an angle from the core well 106 at arcuate intervals of 45 degrees. The four branch wells 108B to E open at the side of ablation electrode 16 and encircle the tip well branch 100A.

A temperature sensing means 84 occupies each branch well 108A to E. In the illustrated and preferred embodiment, a thermal insulating means 88 isolates each temperature sensing means 84 from the interior surface of the associated branch well 108A to E and the remaining thermal mass of the ablation electrode 16.

As in the embodiment Shown in FIGS. 6A to C, each thermal sensing means 84 includes a small bead thermistor 94 with two associated lead wires 96 and 98. The temperature sensing tips of the thermistors 94 are exposed at the tip of the ablation electrode 16 for multiple contact with the tissue. The associated lead wires 96 and 98 are bundled within the center core well 106 and pass through the guide tube 22 to the handle 20.

As in the embodiment shown in FIGS. 6A to C, potting compound 100 encapsulates each thermistor 94 and its lead wires 96 and 98 within the associated branch well. Insulating sheathes 102 also shield the encapsulated lead wires 96 and 98. Together, the compound 100 and sheathes 102 electrically insulate each thermistor 94 from the surrounding ablation electrode 16.

As in the embodiment shown in FIGS. 6A to C, a thermal insulating tube 104 envelopes each electrically encapsulated thermistor 94 and its lead wires 96 and 98. And, as in the FIGS. 6A to C embodiment, adhesive bonds each thermal insulation tube 104 to the interior wall of each branch well 108A to E.

Figure 8A:
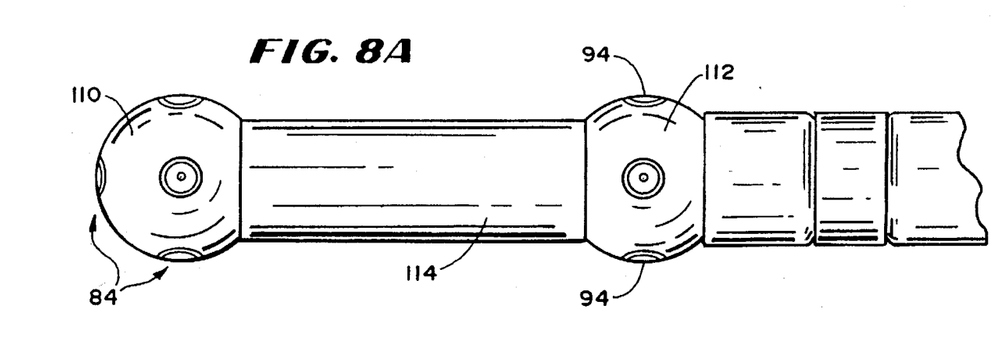
FIGS. 8A to C are views of an electrode specially shaped to use in heart valve regions and having multiple thermally insulated temperature sensing elements that can be used in association with the system to measure tissue temperature.
Figure 8B:
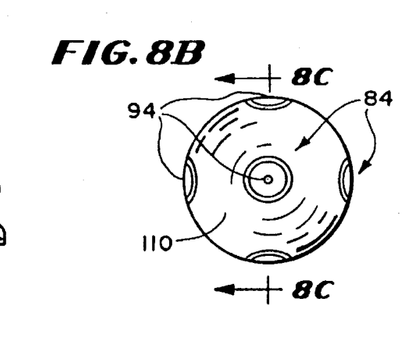
Figure 8C:
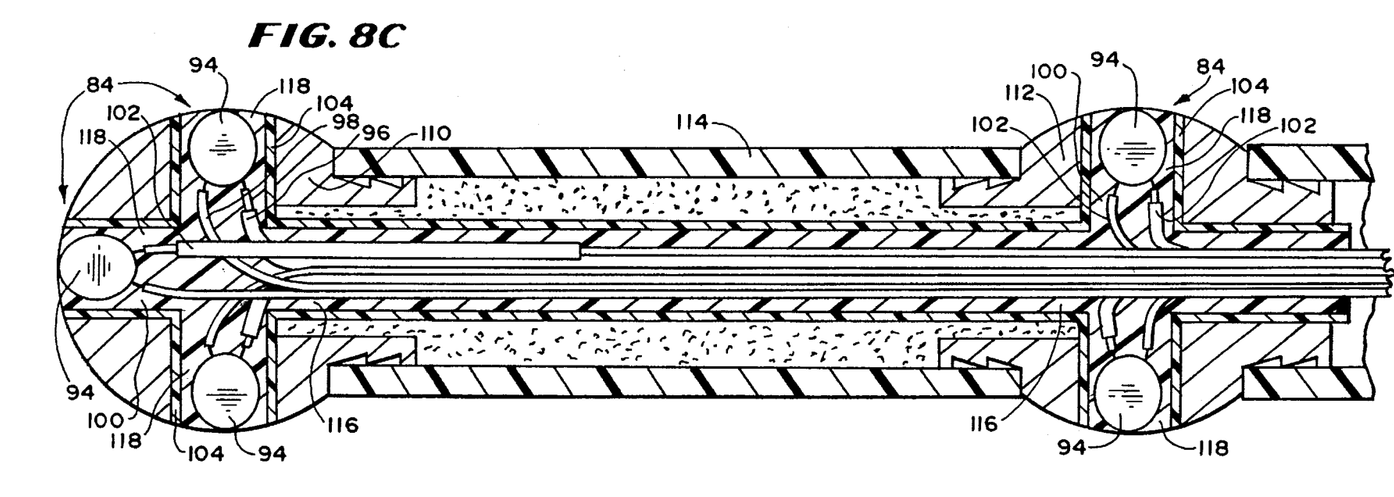

FIGS. 8A to C show another alternate embodiment of an ablation electrode 16 having multiple temperature sensing means 84.

In the arrangement shown in FIGS. 8A to C, the ablation electrode 16 includes a forward electrode region 110 and a rear electrode region 112. The forward electrode region 110 and the rear electrode region 112 are generally spherical in shape.

An electrical and thermal insulating sleeve 114 separates the forward electrode region 110 and the rear electrode region 112. The sleeve 114 is generally cylindrical in shape. The resulting "peanut" shape is well suited for use within the valve regions of the heart.

In the illustrated embodiment, the forward electrode region 110 and the rear electrode region 112 are made of platinum. The sleeve 114 is made of a polysulfone material.

Multiple temperature sensing means 84 occupy the surface of each forward and rear electrode region 110 and 112. At least one, and preferably all, the temperature sensing means 84 are thermally isolated from the remainder of the surrounding body of the associated electrode region 110 and 112.

Each electrode region 110 and 112 includes an interior core well 116 and branch wells 118 that open at the surface of the associated electrode region 110 and 112. A temperature sensing means 84 occupies each well branch. In the illustrated and preferred embodiment, thermal insulating means 88 also isolates each temperature sensing means 84 from the interior surface of the associated branch well 116 and 118 and the rest of the thermal mass of the electrode region 110 and 112.

As in the embodiment shown in FIGS. 6A to C, each thermal sensing means 84 includes a small bead thermistor 94 with two associated lead wires 96 and 98. The temperature sensing tips of the thermistors 94 are exposed at the surface of the associated electrode regions 110 and 112 for multiple contact with the tissue. The associated lead wires 96 and 98 are bundled in the center core well 116, passing through the guide tube 22 to the handle 20.

As in the previous embodiments, potting compound 100 encapsulates each thermistor 94 and its lead wires 96 and 98 within the associated branch well 116 and 118. Insulating sheathes 102 also shield the encapsulated lead wires 96 and 98. Also as in the previous embodiments, a thermal insulating tube 104 envelopes each electrically encapsulated thermistor 94 and its lead wires 96 and 98. Adhesive bonds the thermal insulation tube 104 to the interior wall of each branch well 116 and 118.

The number and arrangement of possible arrays of multiple temperature sensing means 84 can, of course, vary from the specific configurations shown in FIGS. 6, 7, and 8. For example, one or more temperature sensing means 84 can occupy the side region of the ablation electrode 16, below its tip. The branch wells holding the temperature sensing means 84 also can extend from the center well at various angles, acute, obtuse, or perpendicular. Not all the temperature sensing means 84 need be thermally isolated from the electrode 16, but preferable they all are.

As FIG. 5 shows, the third monitoring means 82 can perform different display and control functions in response to sensed temperature conditions according to different prescribed criteria.

Preferably, the third monitoring means 82 responds to sensed tissue temperature not only in absolute terms, but it also serves to record changes in tissue temperature over time and respond to these changes as well.

In the illustrated embodiment, the third monitoring means 82 includes a control output 120 for each temperature sensing means 84 carried by the associated ablation electrode 16.

The lead wires 96 and 98 for each thermistor 94 provide the input for the control outputs 120. Alternatively, when the ablation electrode 16 carries multiple thermistors 94, the number of lead wires 96 and 98 traversing the guide tube 22 can be minimized by providing an integrated circuit 122 within the third monitoring means 82 for multiplexing the input signals of the thermistors 94.

In the illustrated embodiment, the third monitoring means 82 includes a converter 124 to obtain an average temperature for each grouped array of thermistors 94 during a user prescribed period (which in the illustrated embodiment is about once every 0.01 second).

The embodiment shown in FIGS. 6A to C includes one thermistor 94, so the input signal and the average will be the same.

The embodiment shown in FIGS. 7A to C includes a single grouped array of five thermistors 94 clustered at the tip of the ablation electrode 16. For this array, the converter adds the individual input signals and divides by five.

The embodiment shown in FIGS. 8A to C includes two grouped arrays, one having five thermistors 94 on the forward electrode region 110, the other having four thermistors 94 on the rear electrode region 112. The converter 124 adds the input signals for each grouped array and divides by the associated number of thermistors 94 in each grouped array to obtain an average for the forward electrode region 110 and a separate average for the rear electrode region 112.

The third monitoring means 82 includes an analog to digital converter 126. The converter 126 digitizes the sensed temperature average(s) for the system 10.

The converter 126 also digitizes the value of the calibration resistor 134. The thermistor resistance value is divided by the calibration resistor value to get a normalized resistance for the thermistor 94. This value is the input to a read only memory (ROM) 136 (see FIG. 5B) containing stored thermistor temperature data. The ROM 136 output is the actual measured tissue temperature (in degrees C), taking into account deviations in the nominal resistance of the thermistor 94.

Although not shown in the drawings, the embodiments having multiple thermistors 94 would include an equal number of calibration resistors 134, one for each thermistor 94.

The digital output(s) of the converter can be used to display measurement results. In the illustrated embodiment, the system 10 includes a third digital display 128 on the generator 12 to show the user the average sensed temperature.

If the "peanut" type electrode shown in FIGS. 8A to C is used, the system 10 includes a separate display for the forward and rear electrode region 110 and 112.

The digital output(s) of the converter 126 also can be used to control operation of the generator 12. Preferably, the temperature control signals of the third monitoring means 82 also are used to further augment the function of the first and second monitoring means 38 and 76 previously described.

In the illustrated embodiment, the system 10 uses the digitized temperature outputs in a feedback loop that maintains radiofrequency output voltage within a desired range or at a constant value to control radiofrequency power at the ablation electrode 16. By controlling the power delivered by the generator 12 based upon temperature, the physician is able to control the size of the lesion generated.

For this purpose, the system 10 includes an input 130 for the user to enter an operating value desired for the tissue temperature.

If tissue temperature remains within a preset range, but deviates a prescribed amount within the range, the third monitoring means 82 generates a control signal that either increases or reduces but does not interrupt, the power output. If the tissue temperature rises, the control signal reduces the power output. If the tissue temperature falls, the control signal increases the power output. If measured tissue temperature falls outside the preset range, the third monitoring means 82 generates a command signal to shut off power to the ablation electrode 16. A representative set range for tissue temperature for cardiac ablation is believed to be about 40 degrees to 100 degrees C.

When temperature begins in the set range and, over time, fall outside it, the most likely cause is the coagulation of blood on the ablation electrode 16, requiring withdrawal and cleaning of the ablation electrode 16. A sudden change in tissue temperature outside the set range suggests a shift in the position of the ablation electrode 16, requiring repositioning of the ablation electrode 16.

The system 10 preferably includes flashing lights and an audible alarm (not shown) to transmit a warning to the user when these temperature-based conditions occur.

The system 10 as described can provide precise control over the ablation procedure. The monitoring and control of actual phase sensitive power assure the effective distribution of radiofrequency to the ablation electrode 16. The monitoring and control of tissue impedance and tissue temperature, either separately or in combination, set safe physiological limits in terms of lesion size and detection of coagulation. Monitoring and control of tissue impedance and/or tissue temperature also provide information regarding orientation of the ablation electrode 16.

We claim:

1. A system for supplying radiofrequency energy to ablate endocardial tissue, the system comprising electrode means for emitting radiofrequency energy, the electrode means including a distal tip end for contacting endocardial tissue for ablating the tissue, the distal tip end including an open cavity, the electrode means being made of a heat conducting material, temperature sensing means carried within the cavity at the distal tip end of the electrode means, the temperature sensing means including a sensing tip exposed outside the cavity for contact with the tissue that the distal tip end of the electrode means contacts, the sensing tip being operative for sensing tissue temperature contacting the distal tip end of the electrode means while the electrode means emits radiofrequency energy to ablate the tissue, and thermal insulating means filling the cavity around the temperature sensing means for blocking the conduction of heat energy from the electrode means and the sensing tip, generating means connected to the electrode means for conducting radiofrequency ablating energy to the electrode means, control means for the energy generating means including means for registering the temperature of the endocardial tissue being ablated sensed by the temperature sensing means, and means for producing a command signal when the tissue temperature sensed by the sensing means deviates from a predetermined temperature condition.

2. An system according to claim 1 wherein the control means includes means for inputting a prescribed temperature condition.

3. An apparatus according to claim 1 wherein the generating means produces radiofrequency ablating energy at different power levels, and wherein the control means includes means for varying the power level of the generating means in response to the command signal.

4. An apparatus according to claim 3 wherein the command signal increases the power level as the measured tissue temperature decreases toward a prescribed low temperature condition.

5. An apparatus according to claim 3 wherein the command signal decreases the power level as the measured tissue temperature increases toward a prescribed high temperature condition.

6. An apparatus according to claim 3 wherein the command signal interrupts the operation of the generating means.

7. A system for supplying energy to ablate tissue within the heart, the system comprising an electrode element for contacting tissue while emitting energy to ablate the tissue, the electrode element being made of a heat conducting material, a temperature sensing element carried in the electrode element, the temperature sensing element including a sensor having a region for sensing tissue temperature conditions by making thermal conductive contact with tissue, and thermal insulating material in the electrode element around the temperature sensing element, except for the sensor region, for blocking the thermal conduction of heat energy between the electrode element and the sensor to make the sensor region more responsive to sensed tissue temperature conditions than to the thermal mass of the electrode element, generating means connected to the electrode element for conducting ablating energy to the electrode element, control means for the energy generating means including means for registering the temperature of the tissue contacting the sensor, and means for producing a command signal when the tissue temperature sensed by the sensor deviates from a predetermined temperature condition.

8. A system according to claim 7 wherein the control means includes means for inputting a prescribed temperature condition.

9. A system according to claim 7 wherein the generating means produces ablating energy at different power levels, and wherein the control means includes means for varying the power level of the generating means in response to the command signal.

10. A system according to claim 9 wherein the command signal increases the power level as the measured tissue temperature decreases toward a prescribed low temperature condition.

11. An apparatus according to claim 9 wherein the command signal decreases the power level as the measured tissue temperature increases toward a prescribed high temperature condition.

12. An apparatus according to claim 7 wherein the command signal interrupts the operation of the generating means.

13. A system for supplying energy to ablate tissue within the heart, the system comprising an electrode element for contacting tissue while emitting energy to ablate the tissue, the electrode element having a thermal mass, a temperature sensing element carried in the electrode element, the temperature sensing element including a sensor having a region for making thermal conductive contact with tissue to sense tissue temperature conditions, and thermal insulating material in the electrode element between the sensor and the thermal mass of the electrode element, except for the sensor region, for thermally insulating the sensor from the thermal mass of the electrode element to make the sensor region more responsive to sensed tissue temperature conditions than to the thermal mass of the electrode element, generating means connected to the electrode means for conducting ablating energy to the electrode means, control means for the energy generating means including means for registering the temperature sensed by the sensor element, and means for producing a command signal when the temperature sensed by the sensor element differs from a predetermined temperature condition.

14. A system according to claim 13 wherein the control means includes means for inputting the predetermined temperature condition.

15. A system according to claim 13 wherein the generating means produces ablating energy at different power levels, and wherein the control means includes means for varying the power level of the generating means in response to the command signal.

16. A system according to claim 15 wherein the command signal changes the power level as the temperature sensed by the sensor element approaches a prescribed low temperature condition.

17. A system according to claim 15 wherein the command signal changes the power level as the temperature sensed by the sensor element approaches a prescribed high temperature condition.

18. A system according to claim 13 wherein the command signal interrupts the operation of the generating means.

* * * * *